US006322984B1

(12) United States Patent
Preus et al.

(10) Patent No.: US 6,322,984 B1
(45) Date of Patent: Nov. 27, 2001

(54) METHODS INVOLVING NUCLEIC ACID MOLECULES OBTAINED FROM CALCIFIED MICROBIAL CELLS OR MATERIAL EMBEDDED IN DENTAL CALCULUS OF AN ANIMAL

(75) Inventors: Hans R. Preus; Dag Lillehaug, both of Oslo (NO)

(73) Assignee: ADNA AS, Slattum (NO)

( * ) Notice: Subject to any disclaimer, the term of this patent is extended or adjusted under 35 U.S.C. 154(b) by 0 days.

(21) Appl. No.: 09/403,168

(22) PCT Filed: Apr. 14, 1998

(86) PCT No.: PCT/GB98/01083

§ 371 Date: Jan. 18, 2000

§ 102(e) Date: Jan. 18, 2000

(87) PCT Pub. No.: WO98/46791

PCT Pub. Date: Oct. 22, 1998

(30) Foreign Application Priority Data

Apr. 17, 1997 (GB) .................................................. 9707775

(51) Int. Cl.$^7$ ............................. C12Q 1/68; C07H 21/04; G01N 33/48; C12P 19/34; C12P 21/06
(52) U.S. Cl. ........................... 435/6; 435/91.2; 435/40.5; 435/69.1; 435/91.41; 536/25.4; 536/25.41
(58) Field of Search ............................... 536/25.4, 25.41; 435/6, 40.5, 91.2, 69.1, 91.41

(56) References Cited

U.S. PATENT DOCUMENTS 5,989,907 * 11/1999 Boyan et al. ........................ 435/325

FOREIGN PATENT DOCUMENTS

WO 97 25430   7/1997  (WO) .

OTHER PUBLICATIONS

Mukoyama, R. et al. Adv. Forensic Sci. (Proc. Meet. Int. Assoc. Forensic Sci., 13th) 6:256–259, 1995.*
Kawano, S. et al. Nippon Hoigaku Zasshi. Japanese J. Legal Med. 49(3):193–198, Jun. 1995.*
Erlich, H. A. et al. Science 252:1643–1651, Jun. 1991.*
Willett, H.P. Chapter 9, "Antimicrobial Agents", in Zinsser Microbiology, 20th ed., Joklik, W.K. et al, eds., Appleton & Lange, Norwalk, p. 153–187, 1992.*
White, D.J. Eur. J. Oral. Sci. 105:508–522 (1997).*
Takeuchi et al, *Int. J. Urol.,* 3:202–206 (1996).
Takahashi et al, *J. Vet. Med. Sci.,* 57(3):515–517 (1995).
Aass et al, *Scand. J. Dent. Res.,* 102:355–360 (1994).
Rølla et al, *Recent Advances in the Study of Dental Calculus,* J.M. ten Cate, IEL Press, pp. 123–126 (1989).
Glock et al, *J. Dental Res.,* 17:257–264 (1938).
Eggen et al, *Scand. J. Dent. Res.,* 93:426–431 (1985).
Mandel et al, *J. Clin. Peridontol.,* 13:249–257 (1986).
Driessens et al, *Recent Advances in the Study of Dental Calculus,* J.M. ten Cate, IRL Press, pp. 7–17 (1989).
Gaare et al, *J. Dental Res.,* 68(Spec Issue) :1710–1711; Rølla et al (1989).
Petrischev et al, *Genetika,* 29:690–690 (1993), Abstract only.
Hall et al, *Eur. J. Oral Sci.,* 104:285–291 (1996).
Fisher et al, *J. Forensic Sci.,* 38:60–68 (1993).
Hoss et al, *Nucleic Acid Res.,* 21:3913–3914 (1993).
Cattaneo et al, *Forensic Sci. Int.* 74:167–174 (1995).
Laitinen et al, *Biotichniques,* 17:318, 318 and 320–322 (1994).
Simpson et al, *Laryngoscope,* 105;28–34 (1995).
Handt et al, *Experimentia,* 50:534–529 (1994).
Woodward et al, *PCR Methods Appl.,* 3:244–247 (1994).
*Recent Advances in the Study of Dental Calculus,* J.M. ten Cate, IRL Press, pp. 1–4 (1989).

* cited by examiner

*Primary Examiner*—Carla J. Myers
*Assistant Examiner*—Diana Johannsen
(74) *Attorney, Agent, or Firm*—Sughrue, Mion, Zinn, Macpeak & Seas, PLLC

(57) ABSTRACT

The present invention provides the use of animal calculus as a source of nucleic acid which is useful in genetic studies. Such genetic studies may center on the host organism from which the calculus is derived or on microbial organisms whose nucleic acid is embedded in the calculus of the animal host.

20 Claims, 1 Drawing Sheet

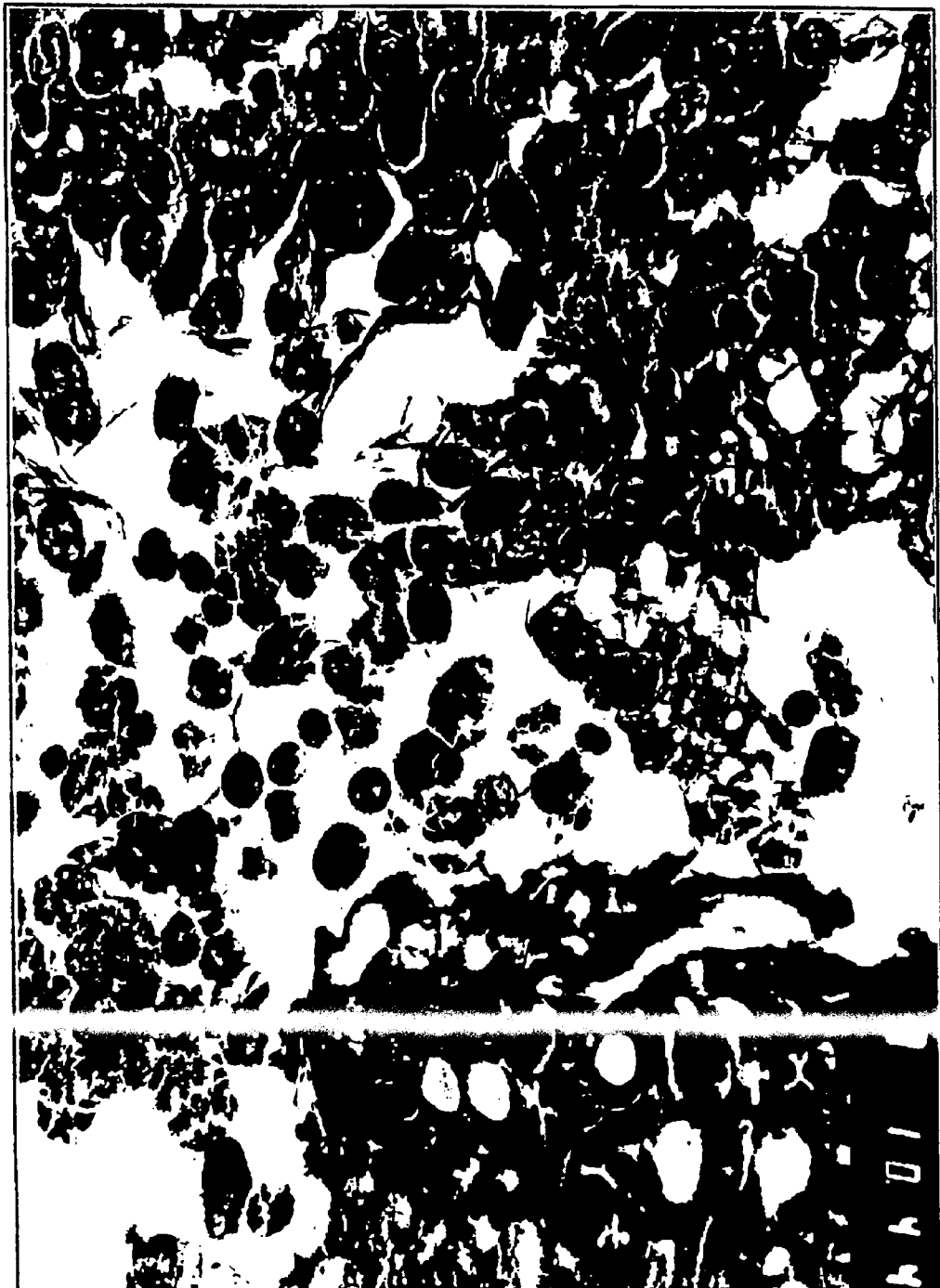

METHODS INVOLVING NUCLEIC ACID MOLECULES OBTAINED FROM CALCIFIED MICROBIAL CELLS OR MATERIAL EMBEDDED IN DENTAL CALCULUS OF AN ANIMAL

This application is the national phase of PCT/GB98/01083, filed Apr. 14, 1998.

FIELD OF THE INVENTION

The present invention relates to the use of calculus as a source of genetic information and in particular to the extraction and characterisation of microbial DNA from the dental calculus of long dead mammals.

DESCRIPTION OF THE RELATED ART

Calculus is a solid mixture of mineral salts, mainly calcium based, which builds up on the surface of teeth and certain other organs, but it may also contain phosphorus, magnesium, fluorine, cobalt, silicon and sodium (Rølla, G. et al., (1989) in Recent Advances in the Study of Dental Calculus Ed. J. M. ten Cate, IEL Press pp 123–126; Glock, G. E. and Murray, M. M. (1938) J. Dental Res. 17:257–264). Dental calculus also comprises an organic phase of bacteria and bacterial remnants, cell products and various compounds found in saliva and gingival fluid (Eggen, K. H., and Rølla, G. (1985) Scand. J. Dent. Res. 93:426–431). Dental calculus may occur supra- and sub-gingivally and there may be differences in the abundance, distribution and structure between the types.

Calculus is found in the ducts, passages, hollow organs, cysts and the surfaces of teeth in humans and other mammals. Calculus persists for many years after the death of the organism and well preserved calculus has been detected, for example, in the teeth of bodies in excess of 5,000 years old. In contrast, all the soft tissues of an organism decompose unless the body is mummified, frozen or otherwise preserved.

Other than its mere existence, most notably on teeth, little is known about the inorganic matrix which constitutes calculus. It is formed by a non-enzymic accumulation of dental plaque, calcium and other mineral salts on a surface which eventually becomes calcified. Nucleators ie. organic or inorganic structures which may serve as templates for deposition of calcium phosphates, are believed to be an important factor in calculus formation and plaque bacteria may play a role. It is widely regarded as an amorphous matrix and most scientific and clinical interest in calculus is directed towards its prevention and removal, since an accumulation of calculus on the teeth is cosmetically undesirable and can result in inflammation of the gums leading to dental problems (Mandel, I. D. and Gaffer, A. (1986) J. Clin. Periodontol, 13:249–257).

It is generally accepted that dental calculus forms to a greater or lesser extent on all mammalian teeth. A major clinical feature of calculus is that it binds tenaciously to the teeth and is difficult to remove. Its formation is spontaneous and effected by diet, chewing behaviour and the microenvironment of the mouth in particular pH. Additionally, there may be some genetic predisposition towards the greater or lesser formation of calculus and certain ethnic groups e.g. Asians, are particularly affected.

pH is a determining factor in the type of calcium salts which predominate in calculus. Animals with a salivary pH of around 8 e.g. dogs and pigs exhibit dental calculus comprising mostly calcium carbonate. Animals with a lower salivary pH of 7, for example, primates including man, exhibit dental calculus based mainly on calcium phosphate deposits (Driessens, F. C. M. & Verbeeck, R. M. H. (1989) In Recent Advances in the Study of Dental Calculus Ed. J. M. ten Cate, IRL Press pp. 7–17).

Similarly, humans with high urinary pH develop urinary calculi comprising mainly calcium carbonate; those with neutral urine develop calculi comprising calcium phosphate and individuals exhibiting low pH urine, who develp calculi, will produce stones rich in uric acid salts.

Diet can affect the formation of calculus in different ways, for example, hard, abrasive foods are believed to assist in preventing calculus formation on the teeth by mechanical agitation.

Dietary silicon can, under certain circumstances promote the formation of urinary calculi in cattle and sheep and there is some suggestion that a high silicon diet, particularly from rice, correlates with increased formation of dental calculus (Gaare, D. (1989) J. Dent. Res. 68:(Spec Issue) 1710–1711; Rølla et al., 1989).

It has recently been shown that calculus on the teeth of both living and long dead people, contains the calcified remains of microorganisms embedded in its matrix. This has not been well researched, but the number and nature of the microorganisms trapped within the calculus appears to be variable. Most bacteria occurring in dental calculus are expected to be plaque bacteria (for example Streptococci and Veillonella) or microorganisms abundant in the buccal flora of the subject. Often, only a single microorganism has been detected, embedded in the calculus matrix.

Surprisingly, not least since microorganisms are present in calculus in such low and variable numbers, it has now been shown that genetic material can be extracted from the calculus of bodies which have been dead for as long as 5,000 years. Even more surprisingly, the isolated nucleic acid, for example from calcified microorganisms embedded in dental calculus, may be isolated in a form amenable to manipulation by recombinant DNA technology and thus may be amplified, sequenced, cloned, expressed, mutated and otherwise manipulated by any molecular biology technique known in the art. Such amenability to manipulation may thus facilitate the study of gene sequences of microorganisms which lived many thousands of years ago.

Although the isolation of genetic material from cells embedded in calculus on archaeological material is a primary feature of the invention, calculus from living animals may also be used as a source of nucleic acid for genetic study.

Whereas dental calculus is believed to harbour only or primarily preserved microbial cells, calculus from other body parts, for example urinary calculi, may also harbour remnants of preserved host cells. In the case where the host has been subjected to infection or where the calculus forms in a body part normally colonised by microorganisms, the calculus may provide a record of host DNA and also DNA from any pathogen, saprophyte or commensal organisms to which the host had been exposed during its lifetime.

SUMMARY OF THE INVENTION

Thus, according to one aspect, the present invention provides the use of animal calculus as a source of nucleic acid.

In particular, the invention provides a useful source of nucleic acid for genetic study.

The calculus may be obtained from any animal body on or in which it is laid down. Conveniently however, the animal will be any mammalian animal.

The calculus may be isolated from any part of the animal, preferably mammalian body.

The nucleic acid may be of host or foreign, eg. microbial origin, and may be DNA or RNA. Preferably, however, it is DNA. More preferably if the DNA is of eukaryotic origin, it is nuclear DNA.

BRIEF DESCRIPTION OF DRAWING

FIG. 1 shows an electron micrograph of a section of calculus taken from the teeth of a 5,000 year old body, believed to be that of an ancient Norwegian farmer. The round structures are calcified microorganisms. Magnification is 10,000×.

DESCRIPTION OF THE PREFERRED EMBODIMENTS

In a preferred aspect of the invention, the genetic material is from microorganisms which may be isolated from calculus, formed during the life of the host, on or in any part of the body. A particularly advantageous feature of the present invention is that the microbial material isolated from the calculus, may comprise ancient microorganisms. In other words the host body, from which the calculus is obtained may have been long dead. Thus, the calculus may be obtained not only from intact bodies which may be dead or alive but also from skeletal remains.

The invention thus encompasses the use of a living animal body as a source of the calculus, or a dead body, which may be recently or long dead. The dead body may be intact in its entirety, or body parts may be used, with varying degrees of decomposition. Skeletal material devoid of soft tissue may be used. "Long dead" ads used herein encompasses anything from tens to thousands of years from death. In other words, the body or body part, from which the calculus is obtained, may have died from 1 day up to 20,000 years or more ago, and preferably, up to 10,000 years ago. The invention thus lends itself well to the study of archaeological or archive material.

In a particularly preferred aspect, the calculus from which the nucleic acid is isolated is dental calculus.

Alternatively viewed, a preferred aspect of the invention can thus be seen to provide a method of obtaining microbial nucleic acid, characterised in that the said nucleic acid is derived from microorganisms contained in the calculus of an animal host.

The term "microorganism" is used within the context of this application to cover all microbial organisms or cellular material and in particular bacteria, fungi and viruses as well as plant cells such as algae including blue-green algae, and protozoa. Spores from sporulating bacteria or fungi are also within the scope of the term microorganism as are plasmids, bacteriophage and mycoplasmas.

In terms of microorganisms associated with the mammalian body, they may be of any species or genus and of course may be commensals, pathogens or saprophytes.

Although this represents a preferred aspect, the invention is not limited to isolating the nucleic acid of microorganisms from calculus, and the nucleic acid may be obtained from any cells or cellular material eg. organelles which are contained in the calculus, including all eukaryotic cells which may be plant or animal cells or protoplasts, and include the cells of the host.

Genetic information gleaned by the study of nucleic acids obtained from calculus is very useful to the pharmaceutical industry, by providing sequence data from microorganisms which existed prior to the advent of antibiotics, biocides or other means for the control of microbial activity and hence prior to the emergence of antibiotic resistance. Such information may add to the understanding of the evolution of resistance mechanisms and augment the development of new strategies and formulations for overcoming and/or avoiding the development and spread of drug resistance.

It is believed that ancient microorganisms themselves produced substances, for example metabolites or enzymes, with antimicrobial properties which provided them with a competitive advantage against other microorganisms. Identifying such products from expressing cloned genes from the ancient microorganisms, may provide novel anti-microbial products, useful in themselves. It will be understood by the skilled person that such novel gene products may find many applications in a diverse range of scientific areas. Of particular interest however is the potential such compounds have for counteracting multiple drug resistance in present day pathogenic organisms which will never have been exposed to such compounds.

Replacement therapy is viewed by many as being a new approach to combatting infection and the use of genetic information from calculus derived microorganisms could provide significant advances in this regard.

As mentioned above, calculus may form and harbour microorganisms on body parts exposed to microbial infection, or in areas normally colonised by microorganisms. Thus, genetic information about microorganisms with specific habitats or infection sites for example, coliforms or enteric pathogens in the gastrointestinal tract, Streptococci or Mycobacteria in the lungs or Staphylococci in the urinary tract may be generated and the information used by the pharmaceuticals industry in the avoidance of antibiotic resistance, replacement therapy and for the expression of novel products as described above.

Furthermore, it is thought that insofar as dental calculus is concerned, microorganisms responsible for many disease processes, not only those limited to the buccal cavity or gastrointestinal tract, may be represented in the calculus matrix.

In addition to the commercial, pharmaceutical benefits provided by use of the present invention, the information gained from calculus-derived microbial genetic information may be useful in the study of population movement and interaction in groups of people and animals thousands of years ago.

Also, it may provide answers to many questions which still surround ancient epidemiological riddles. For example, it is still not certain which microorganism(s) was the cause of the "black plague" which killed large numbers of people in continental Europe in the 12th century. Since the soft tissues of all the people killed by the plague were actively destroyed, there is no identifiable repository of the organisms which killed the victims available for studies. It is proposed herein however, that study of the organisms and genetic material therein, embedded within the dental or other body calculus of the victims of the plague or other diseases, will yield an identity and characteristics of the microorganism(s) responsible.

In addition to the clear scientific and anthropological interest this would generate, such studies may also yield valuable epidemiological data useful for today's understand of the spread of disease within populations and therefore provide means for its circumvention.

In a further preferred aspect therefore, the calculus from which microbial DNA is extracted is of human origin.

A particular advantage of using dental calculus as a source of microbial DNA is that it does not contain significant amounts of host DNA and hence the study of ancient microbial DNA is not complicated by host DNA contamination.

The resilience of calculus to degradation means that even on body remains which have been burnt and subject to exposure to the elements for millennia, there is effectively no age limit to the samples which may usefully provide genetic information.

Viewed from a further aspect, the present invention provides a method of study of microbial genetics characterised in that microbial nucleic acids for said study are derived from animal calculus.

The term "genetic study" is used herein in its broadest sense to encompass all forms of study or analysis related to the genome, including not only epidemiological studies and comparisons between different organisms, or organisms obtained from different sources of calculus eg. animals from different locations or of different species, but also any study or manipulation of the isolated genetic material itself eg. sequencing, cloning, expression, modification, amplification etc. Many techniques for genetic study are described for example by Sambrook et al., in "Molecular Cloning", a Laboratory manual, 2nd Edition, Cold Spring Harbour Laboratory Press, 1989.

The term "derived" is used herein to include not only obtaining or isolating the nucleic acid directly from the calculus, but also nucleic acid derived by copying or amplifying the originally isolated source nucleic acid.

Also provided according to the invention is a method of comparing nucleic acids from different individuals, characterised in that the nucleic acids are derived from animal calculus. Preferably, the nucleic acids are derived from microorganisms within the calculus.

The "individuals" may be any animal, but advantageously will be human. The nucleic acids derived from the calculus may be compared using any of the techniques for genetic study which are well known in the art and widely described in the literature eg. by in vitro amplification eg. by PCR and subsequent analysis of the amplification products eg. by size fractionation by gel electrophoresis, restriction fragment length polymorphism analysis (RFLP), hybridisation-based methods, sequencing, etc.

Presently, where mummified or frozen remains of soft tissues exist, it is possible to identify and study genetic information from the host and also any organisms remaining in the soft tissues. Where no soft tissue remains exist however this is clearly not possible. If however calcified material can be identified within the body cavity ie. calculus, it would be possible using the present invention to identify and characterise the genetic information from both the host and any microorganisms present.

Hence, in a further aspect, the present invention provides the use of calculus originating from an animal host body as a source of genetic information derived from the host. The calculus may conveniently be from the ducts, passages, hollow organs and cysts which form within the animal body. Where the host animal has been subject to infection or normal microbial colonisation, calculus derived from tissues such as e.g. the ducts, passages, hollow organs and cysts may further provide a source of genetic information of those organisms.

The methods employed in the extraction, characterisation and molecular manipulation of the extracted genetic information may all be performed by techniques used in the art and a process for the preparation of isolated nucleic acids of host or microbial origin is provided herein, characterized in that the nucleic acids are derived from animal calculus.

One possibility for extracting nucleic acids from calculus involves isolating the calculus from the body and washing it with antimicrobial agents to remove surface contamination. The calculus is then pulverised and the nucleic acid trapped therein is eluted by water. A similar technique for extracting DNA from bone and teeth has been previously described by Petrischev, V. N. et al., (1993) Genetika 29;690–693.

Another approach is to subject the washed calculus to a process of demineralisation by suspending the isolated calculus in an aqueous solution comprising EDTA, or a similar chelator of divalent cations, which binds calcium ions, the major substituent of calculus, and magnesium ions. Chelation of magnesium ions inhibits DNAse enzyme activity which would degrade the DNA. A similar approach has been described by Hall, R. C. et al., (1996) Eur. J. Oral Sci. 104:285–291, in the extraction of native DNA from teeth.

Alternatively, it has been shown by Fisher, D. L. et al., (1993) J. Forensic Sci. 38:60–68, that it is possible to apply DNA extracted from undecalcified material directly to a PCR reaction mixture. Furthermore, the yield of DNA extracted from undecalcified material was double that from decalcified material. An analogous process may be applied to calculus.

DNA within the calculus may be amplified in situ using PCR. The resultant fragments may be hybridised in situ and visualised or may be extracted and purified. This technique involves sectioning the calculus in a similar manner to that used for electron microscopy and then creating a PCR reaction chamber on a glass slide by adding the PCR mixture to the section under analysis and enclosing the mixture using a rubber seal. The PCR reaction may then be carried out as appropriate.

Silica based purification methods as, for example, described by Hoss, M. & Paabo, S. (1993) Nucleic Acids Res. 21:3913–3914, may also be used successful in the extraction of nucleic acid from calculus.

Yet a further possibility may be the breaking down of silicate junctions which form the cornerstones of calculus by using weak acids and extracting the nucleic acids therefrom.

Other methods which may be used or adapted for use in extracting nucleic acids from calculus include the procedures discussed by Cattaneo, C. et al., (1995) Forensic Sci. Int. 74:167–174; Laitinen, J. et al., (1994) Biotichniques 17:316, 318, 320–322; Simpson, T. A. & Smith, R. J. (1995) Laryngoscope 105:28–34. Any method described in the literature, for example, for extracting nucleic acids from bones or skeletal material could be used, for example, techniques which break down silicate junctions of calcified material and of particular interest are techniques specifically adapted for use with ancient material, as described for example, by Handt, O. et al., (1994) Experimentia 50:534–529, or Woodward, S. R. et al., (1994) PCR Methods Appl. 3:244–247.

Thus, although the nucleic acids may be extracted by any known methods, methods in which an appreciable amount of nucleic acid is lost during the extraction and purification process for example, those involving solvent extraction e.g. phenol/chloroform extraction, precipitation for example using precipitants such as salts, or the binding of nucleic acid to various types of matrices are less preferred, since it is desirable to perform the purification with as little loss as possible.

It is desirable that the methods employed to extract and purify the nucleic acid should result in minimal amounts of degradation and/or loss of DNA. This is important since the amount of DNA or other nucleic acid available for study may be small.

In combination with any extraction method employed, it may be advantageous to disrupt any microbial cell walls which remain intact within the calculus matrix. This may be done via a series of boiling and freezing (in liquid nitrogen) steps or by using enzymic degradation, for example lysozyme and/or mutanolysine and a proteinase such as Proteinase K. Other methods exist in the art which are suitable for removing or disrupting cell walls or achieving cell lysis as will be easily recognised by the skilled person.

Once in solution, residual enzymes may be inactivated by boiling and salts, for example EDTA, may be removed by dialysis or similar procedure if desired. The DNA may then be concentrated by dehydration. Optionally, extracted nucleic acids may be run through an agarose gel by electrophoresis prior to subjecting them to PCR or other manipulations, since this has the effect of removing most inhibitors of the PCR or other reactions. Clearly, this may not always be possible when working with very small samples.

PCR amplification and any other techniques known and used within molecular biology may then be used to amplify, sequence, clone, manipulate and express the DNA. PCR primers, for example, suitable for species identification and classification may be designed and the purified DNA applied directly to a PCR reaction mixture. The resultant products of the PCR reaction may then be sequenced to allow identification and initial characterization of the origin of the DNA in question. Any of the techniques known in the art and described in the literature for the manipulation or detection of nucleic acids may be used, including in addition to any of the in vitro amplification methods or sequencing methods, methods for detecting point or other mutations, base transitions etc.

In addition to extraction, amplification and manipulation procedures of chromosomal DNA, human genetic information derived from host cell remnants are amenable to techniques such as mitochondrial DNA sequence analysis.

Alternatively, nucleic acid may be studied in situ ie. directly on the calculus material, by sectioning the calculus using micro-manipulation techniques, or it may be studied by extracting the nucleic acid from individual cell remnants per se and then purifying it.

The invention will now be described in more detail by way of the following non-limiting examples with reference to the drawing in which FIG. 1 shows an electron micrograph of a section of calculus taken from the teeth of a 5,000 year old body, believed to be that of an ancient Norwegian farmer. The round structures are calcified microorganisms. Magnification is 10,000×.

EXAMPLE 1

Dental calculus was isolated mechanically from the teeth of a 5,000 year old non-mummified skeleton, thought to be that of a farmer. The calculus was washed in an antimicrobial solution to clean the surface, crypts and ducts and remove contaminants. It was washed again and then sectioned using standard techniques for electron microscopy studies. Electron micrographs show bacteria embedded within the calculus (see FIG. 1). The bacteria within the calculus are observed as round bodies and the morphology of the microorganisms is well preserved.

EXAMPLE 2

Extraction of DNA From the Calculus

The calculus is carefully scraped from the surface of the teeth and washed as described in Example 1. The calculus is suspended in 250 mM EDTA (pH 8.0) containing 20 mg/ml lysozyme and 1200 units/ml mutanolysine. The mixture is incubated for 30 minutes at 37° C. and then SDS and proteinase-K are added to a final concentration of 0.1% and 50 µg/ml, respectively. The mixture is incubated for a further 30 minutes at 65° C. The mixture is subjected to 5 sequential cycles of boiling for 1 minute followed by freezing in liquid nitrogen for 1 minute. The resultant liquid is dialysed for 30 minutes on a filter against a 10 mM tris buffer (pH 8.0; on a petri-dish). The nucleic acid containing liquid is transferred to an Eppendorf tube and the nucleic acid dehydrated by vacuum (in a "speedvac"). The dehydrated samples are resuspended in an appropriate volume of $dH_2O$ (5–20 µl).

DNA prepared by this method may then be applied directly to PCR reaction mixture for PCR amplification. Resultant strands of DNA may be separated by agarose-gel-electrophoresis and purified therefrom by standard methods and the purified DNA sequenced.

What is claimed is:

1. A method selected from the group consisting of:

(i) a method comprising the step of isolating nucleic acid molecules from calcified microbial cells embedded in dental calculus of an animal, or from calcified microbial cellular material embedded in said dental calculus, and optionally, thereafter copying the resulting isolated nucleic acid molecules; and (ii) a method comprising the step of amplifying in situ nucleic acid molecules from calcified microbial cells embedded in dental calculus of an animal, or from calcified microbial cellular material embedded in said dental calculus, and optionally isolating the resulting amplified nucleic acid molecules.

2. The method (i) as claimed in claim 1, wherein said copying is achieved by amplifying the resulting isolated nucleic acid molecules.

3. The method (i) as claimed in claim 1, wherein said isolating nucleic acid molecules is carried out by the steps of:

(A) isolating dental calculus from an animal; and (B) extracting nucleic acid molecules from calcified microbial cells embedded in the resulting isolated dental calculus or from calcified microbial cellular material embedded in the resulting isolated dental calculus so as to isolate said nucleic acid molecules.

4. The method as claimed in claim 1, wherein said animal is a mammal.

5. The method as claimed in claim 4, wherein said mammal is a human.

6. The method as claimed in claim 1, wherein said nucleic acid molecules are DNA molecules.

7. The method as claimed in claim 6, wherein said DNA molecules are nuclear DNA molecules.

8. The method as claimed in claim 1, wherein said calculus is calculus formed while said animal was alive.

9. The method as claimed in claim 1, wherein said animal has been dead for up to 20,000 years.

10. The method as claimed in claim 9, wherein said animal has been dead for 500 to 10,000 years.

11. The method as claimed in claim 9, wherein said calculus is from skeletal remains of said animal.

12. The method as claimed in claim 10, wherein said calculus is from skeletal remains of said animal.

13. The method as claimed in claim 1, wherein said microbial cells are selected from the group consisting of bacterial cells, fungal cells, viruses, algal cells, blue-green algal cells, protozoal cells, microbial cells comprising bacteriophage, and mycoplasmas.

14. The method as claimed in claim 13, wherein said microbial cells are a causative agent of disease.

15. The method as claimed in claim 14, wherein said microbial cells are selected from the group consisting of coliform cells, enteric pathogen cells, streptococcal cells, mycobacterial cells and staphylococcal cells.

16. The method as claimed in claim 1, wherein said nucleic acid molecules encode a gene product selected from the group consisting of an anti-microbial gene product, an antibiotic resistance gene product, and a gene product associated with antibiotic resistance.

17. The method of claim 1, wherein the resulting isolated, copied or amplified nucleic acid molecules are subjected to genetic analysis.

18. The method of claim 17, wherein said genetic analysis is an epidemiological analysis.

19. The method of claim 17, wherein said genetic analysis comprises comparing nucleic acid molecules from dental calculus of different individual animals.

20. The method of claim 1, wherein the resulting isolated, copied or amplified nucleic acid molecules are subjected to cloning, and optionally a gene product encoded by the resulting cloned nucleic acid molecules is expressed, and optionally the gene product is isolated.

* * * * *